United States Patent [19]

Buchman

[11] 4,234,514

[45] Nov. 18, 1980

[54] METHOD OF PREPARING KETOXIME CARBAMATES

[75] Inventor: Russell Buchman, Madison, Ohio

[73] Assignee: Diamond Shamrock Corporation, Dallas, Tex.

[21] Appl. No.: 966,389

[22] Filed: Dec. 4, 1978

[51] Int. Cl.³ ............................................. C07C 131/00
[52] U.S. Cl. .................................................... 564/255
[58] Field of Search ..................... 260/566 AC, 566 A

[56] References Cited

U.S. PATENT DOCUMENTS

| 3,832,400 | 8/1974 | Meyer et al. | 260/566 A |
| 3,873,624 | 3/1975 | Mathew et al. | 260/566 A |
| 3,875,232 | 4/1975 | Magee | 260/566 AC |

OTHER PUBLICATIONS

Iffland, Don C. et al. "The Preparation of Nitro Compounds from Oximes", Parts I and II, J. of the American Chemical Society, vol. 75, (1953) pp. 4044–4046 and 4047–4048.

Diekmann H. et al. "A Productive Method for the Preparation of Geminal Chloronitroso Compounds," Angew. Chem. Internat. Ed. vol. 7 (1963) pp 387–388.

*Primary Examiner*—Natalie Trousof
*Assistant Examiner*—L. Hendriksen
*Attorney, Agent, or Firm*—John C. Tiernan; John J. Freer

[57] ABSTRACT

A novel process of preparing ketoxime carbamate.

3 Claims, No Drawings

METHOD OF PREPARING KETOXIME CARBAMATES

BACKGROUND OF THE INVENTION

The present invention relates to the synthesis of organic compounds, and, more particularly, to the synthesis of certain ketoxime carbamates.

U.S. Pat. No. 3,875,232 and a number of subsequent related United States patents have issued to Thomas A. Magee disclosing and claiming certain novel ketoxime carbamate compositions. These compositions are described by the formula:

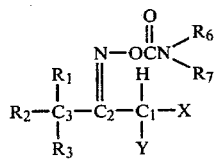

where:
$R_1$ = hydrogen, $R_2$-$R_3$ or X;
$R_2$-$R_3$ = lower alkyl, lower alkenyl, lower alkynyl, substituted lower alkyl, alkenyl, or alkynyl with the proviso that $R_2$ and $R_3$ may be connected to form a cycloaliphatic ring;
$R_6$-$R_7$ = hydrogen, lower alkyl, lower alkenyl, or lower alkynyl;
Y = H or X;
X = is selected from the group consisting of $SR_8$, $S(O)R_8$, $SO_2R_8$, $OR_8$, $OSO_2R_8$, $NR_8R_9$, $NO_2$, CN, SCN, $N_3$, or halogen with the proviso that when X and Y are $OR_8$, $SR_8$, $S(O)R_8$, $SO_2R_8$, or $NR_8R_9$, X and Y may be connected to form a heterocyclic ring;
$R_8$ = hydrogen, lower alkyl, lower alkenyl, lower alkynyl, aryl, substituted aryl, carbamyl, substituted carbamyl, acyl, or substituted acyl with the proviso that the lower alkyl or alkenyl groups may be further substituted with X; and
$R_9$ = hydrogen or lower alkyl with the proviso that $R_8$, $R_9$ and N in the $NR_8R_9$ group may form a heterocyclic ring.

The term lower alkyl radical means a radical having from one to about seven carbon atoms.

According to Magee, the compounds can be prepared by one of three basic methods. The first method (referred to by Magee as Method A) involves reaction of an isocyanate with an oxime as shown, for example, in the equation:

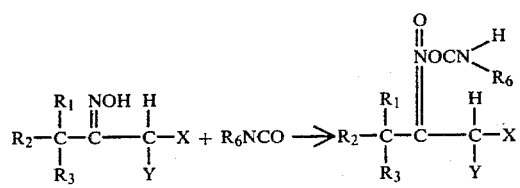

wherein $R_1$ through $R_6$ and X are defined above. The oxime and isocyanate are reacted in an inert organic solvent from about 0° C. to about 150° C., preferably from about 20° C. to about 80° C., and at a pressure from about 1 to 10 atmospheres, preferably from about 1 to about 3 atmospheres. Reaction pressure is determined by reaction temperature, concentration and vapor pressure of the isocyanate. Preferably, reaction is carried out in the presence of from about 0.1 to about 1.0 percent, by weight, based on the weight of reactants, of a tertiary amine catalyst such as triethyl amine, N,N-dimethylaniline, or the like. The molar ratio of isocyanate to oxime can vary from about 0.1:1 to about 10:1. An equimolar amount or slight excess of isocyanate is preferred to ensure complete reaction of the oxime. Reaction times can vary from a few minutes to several days. Usually, reaction times of from about one-half to about six hours are sufficient.

A second method (referred to by Magee as Method B) involves reaction of an oxime with phosgene to obtain an oxime chloroformate which is then reacted with an amine. This method is illustrated in Equations (1) and (2) below:

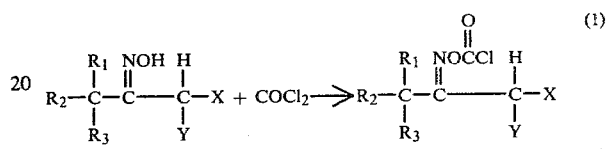

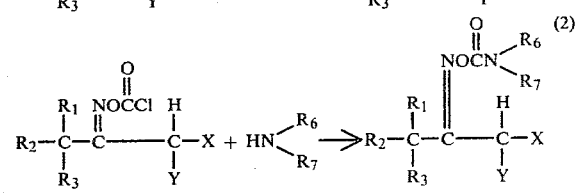

In the reaction shown in Equation (1), a solution of the oxime dissolved in an inert solvent as diethyl ether, is added slowly to a solution of phosgene dissolved in an inert solvent in the presence of an HCl acceptor such as a tertiary amine, e.g., N,N-dimethylaniline. Reaction is carried out from about −30° C. to about 100° C., preferably at from about 0° C. to about 50° C. The resulting reaction mixture, a solution of the chloroformate in an inert organic solvent, can be filtered or washed with water to remove amine hydrochloride before it is used in the reaction shown in Equation (2).

In the reaction shown in Equation (2), an amine is added to the chloroformate solution in the presence of an amine solvent such as water, at temperatures between about −40° C. and about 80° C., preferably at about 0° C. to about 40° C. A larger than molar excess of amine can be used so that the amine acts both as reactant and as HCl acceptor and complete conversion of chloroformate is obtained. Alternatively, a separate HCl acceptor, such as tertiary amine, can be used.

The third method (referred to by Magee as Method C) for the preparation of such compositions comprises reacting:

(a) a compound of the formula

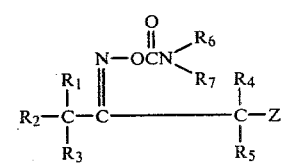

wherein Z is a reactive halogen, and
(b) HX,
in the presence of an HZ acceptor. This includes reaction of the haloketones with mercaptans or alcohols in the presence of an acid acceptor, e.g., sodium alkoxide.

Sulfinyl and sulfonyl linked compounds can be prepared by oxidizing the appropriate sulfide linked compound with sodium metaperiodate or acidic hydrogen peroxide, respectively.

In most of the compounds prepared by Magee using the three above-described procedures, Y was hydrogen. Attempts to employ these procedures to synthesize compounds in which Y was a second X group using Method C produced only very small yields because of the number and variety of side reactions, and the oxime starting materials were not available for Methods A or B.

Another potential method of producing compounds where $R_5$ is a second X moiety, would seem to be the oximation of 2-keto-1,1-dithioacetals as illustrated by the equation:

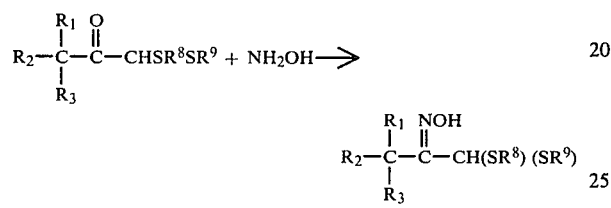

However, this method also has a limited success apparently because of the steric hinderance of the dithioacetal group as confirmed by P. E. Pearson and O. D. Keaton in a 1963 article in the *Journal of Organic Chemistry*, Volume 28, page 1557.

SUMMARY OF THE INVENTION

I have now discovered that compounds of the formula:

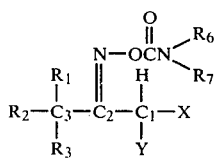

where:

$R_1$ = hydrogen, $R_2R_3$ or X;

$R_2$-$R_3$ = lower alkyl, lower alkenyl, lower alkynyl, substituted lower alkyl, alkenyl, or alkynyl with the proviso that $R_2$ and $R_3$ may be connected to form a cycloaliphatic ring;

$R_6$-$R_7$ = hydrogen, lower alkyl, lower alkenyl, or lower alkynyl;

X-Y = X and Y may be the same or different and each is selected from the group consisting of $SR_8$, $S(O)R_8$, $SO_2R_8$, $OR_8$, $OSO_2R_8$, $NR_8R_9$, $NO_2$, CN, SCN, $N_3$, or halogen with the proviso that when X and Y are $OR_8$, $SR_8$, $S(O)R_8$, $SO_2R_8$, or $NR_8R_9$, X and Y may be connected to form a heterocyclic ring;

$R_8$ = hydrogen, lower alkyl, lower alkenyl, lower alkynyl, aryl, substituted aryl, carbamyl, substituted carbamyl, acyl, or substituted acyl with the proviso that the lower alkyl or alkenyl groups may be further substituted with X; and $R_9$ = hydrogen or lower alkyl with the proviso that $R_8$, $R_9$ and N in the $NR_8R_9$ group may form a heterocyclic ring.

wherein the term lower alkyl radical means a radical having from one to about seven carbon atoms can be synthesized by preparing a compound of the formula:

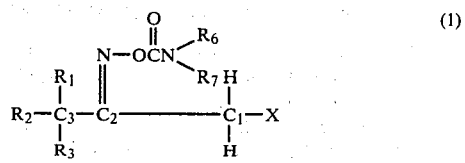

Such compounds can, of course, be prepared according to the teaching of U.S. Pat. No. 3,875,232 (the specification of which is specifically incorporated herein by reference) and halogenating said compound to form the halogenated intermediate having the formula:

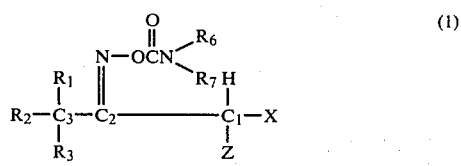

wherein Z is a reactive halogen and reacting said intermediate with HY in the presence of an HZ acceptor.

In other words, I have found that while it is difficult to form the doubly halogenated intermediate for use with Magee's Method C, e.g., a compound of the formula:

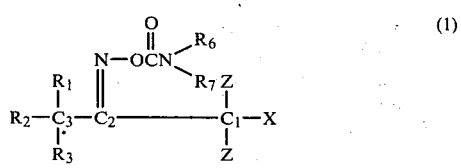

it is possible to form the desired ultimate compositions by employing two successive halogenation procedures. That a significant degree of halogenation takes place on the selected carbon atom, and not elsewhere in the structure is highly unexpected.

DESCRIPTION OF THE PREFERRED EMBODIMENT

The preferred embodiment of the present invention comprises halogenating a compound of the formula:

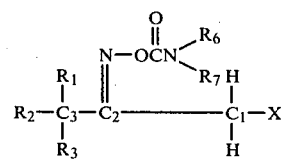

wherein $R_1$-$R_7$ are as defined hereinbefore and X is $S(O)_nR_8$ and reacting the halogenated intermediate with a compound of the formula HY. The reaction conditions are otherwise as described in U.S. Pat. No. 3,875,232. The following examples will serve by way of illustration and not by way of limitation to describe the process of the present invention.

Compound No. 7268, 3,3-dimethyl-1-methylthio-2-butanone which is disclosed in U.S. Pat. No. 3,875,232 was prepared as follows:

EXAMPLE 1

3,3-dimethyl-2-methylcarbamyloximino-1-methylthiobutane (Compound 7268)

Compound No. 7268 was prepared using the following procedure:

3,3-dimethyl-1-methylthio-2-butanone

To a solution of sodium ethoxide prepared from 7.7 g (0.33 mol) of sodium metal and 200 ml of absolute alcohol was added 19 g (0.4 mol) of methanethiol over 10 min. at ±2° C. To this solution of thiomethoxide was added dropwise, over 25 min., 59 g (0.28 mol) of 1-bromo-3,3-dimethyl-2-butanone prepared according to the procedure of J. Am. Chem. Soc. 74, 4507 (1952). The temperature was maintained at 0°±3° C. during the addition and for a further 30 min. The reaction mixture was filtered and the solvent removed by distillation. Vacuum distillation of the residue gave the desired product as a colorless liquid, b. 73° C./9.3 mm Hg, $n_D^{24} 1.4650$ in 54 percent pure yield.

3,3-dimethyl-1-methylthio-2-butanone oxime

A solution of 20.4 g (0.14 mol) of 3,3-dimethyl-1-methylthio-2-butanone, 19.6 g (0.28 mol) of hydroxylamine hydrochloride and 14.8 g (0.14 mol) of anhydrous sodium carbonate in 140 ml of 95 percent ethanol and 80 ml of water was heated at reflux for 16 hrs. The resulting nearly colorless solution was stripped of volatiles on a rotary evaporator to yield a two layered liquid residue. This residue was extracted with four portions of ethyl acetate. The organic extract was dried over magnesium sulfate, filtered from the drying agent and stripped of solvent. Distillation of the residue gave the desired product as a colorless liquid, b. 83° C./0.6 mm Hg, $n_D^{22} 1.4989$.

Calc'd for $C_7H_{15}NOS$: C, 52.1; H, 9.4; N, 8.7; Found: C, 52.2; H, 9.4; N, 8.6.

3,3-dimethyl-2-methylcarbamyloximino-1-methylthiobutane

A solution of 110 g (0.68 mol) of 3,3-dimethyl-1-methylthio-2-butane oxime, 42.8 g (0.75 mol) of methyl isocyanate and three drops of triethylamine in 400 ml of anhydrous acetone was heated at reflux for 16 hrs. Volatiles were removed by stripping on a rotary evaporator to give 155 g of white solid residue, m 50°-53° C. A solution of 25 g of this residue in 200 ml of ether was washed with two 100 ml portions of water. The dried ether solution was reduced in volume to yield 12.6 g of white crystal, m 56.5°-57.5° C., which is the desired compound.

Calc'd for $C_9H_{18}N_2O_2S$: C, 49.5; H, 8.3; N, 13.0; Found: C, 49.3; H, 8.9; N, 12.9.

Using the 3,3-dimethyl-1-methylthio-2-butanone prepared in Example 1, 3,3-dimethyl-1-methoxy-1-methylthiobutane-2-one O-(N-methylcarbamoyl)oxime is prepared.

EXAMPLE 2

3,3-dimethyl-1-methoxy-1-methylthiobutane-2-one O-(N-methylcarbamyl)-oxime

To a stirred solution of 3,3-dimethyl-1-methylthiobutane-2-one O-(N-methylcarbamyl)-z-oxime (2.18 g, 0.01 mole) and carbon tetrachloride (25 ml) was added N-bromosuccinimide (1.78 g, 0.01 mole) in one portion at room temperature.

The resulting mixture was stirred overnight at room temperature, filtered and the filtrate evaporated in vacuo to a yellow syrup. The syrup was dissolved in absolute methanol (25 ml) and the resulting solution was stirred at room temperature for 1 hour. Sodium (0.24 g, 0.01 mole) was then added in one portion and the resulting mixture stirred at room temperature for 2 hours. The resulting solution was evaporated in vacuo, the residue extracted with chloroform and the combined extracts evaporated in vacuo to a syrup. The syrup was applied to a dry column of silica gel and eluted with anhydrous diethyl ether. A clear, colorless syrup (0.8 g) was obtained which crystallized with scratching after standing at room temperature for approximately four weeks. The structure was established by means of NMR and IR spectra.

In general, the sulfide compounds of the present invention will be oxidized, in situ during use, to the corresponding sulfoxide and then to the corresponding sulfone. The oxidation can also be achieved by direct synthesis, as illustrated by Example 8 of U.S. Pat. No. 3,875,232.

It will be apparent to those skilled in the art that many alterations and changes can be made in the materials, compounds and procedures hereinbefore without departing from the topic of the present invention, and it is my intention it be limited only by the appended claims.

What is claimed is:

1. A method of preparing compounds at a temperature from about 0° C. to about 150° C. of the formula:

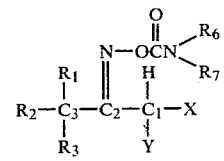

where:

$R_1$ = hydrogen, $R_2R_3$ or X;

$R_2$-$R_3$ = lower alkyl, lower alkenyl, or lower alkynyl, with the proviso that $R_2$ and $R_3$ may be connected to form a cycloaliphatic ring;

$R_6$-$R_7$ = hydrogen, lower alkyl, lower alkenyl, or lower alkynyl;

X-Y = X and Y may be the same or different and each is selected from the group consisting of $SR_8$, $S(O)R_8$, $SO_2R_8$, $OR_8$, or $NR_8R_9$;

$R_8$ = hydrogen, lower alkyl, lower alkenyl, lower alkynyl, or aryl; and $R_9$ = hydrogen or lower alkyl which comprises halogenating a compound of the formula:

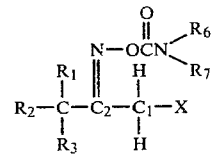

to form a halogenated intermediate, and reacting said intermediate with a compound of the formula HY in the presence of a hydrogen halide acceptor.

2. The process according to claim 1 where said reaction is carried out in an inert solvent.

3. The process according to claim 1 where X is $S(O)_nR_8$ and n is 0, 1 or 2.

* * * * *